US010298849B2

(12) United States Patent
Yoo et al.

(10) Patent No.: US 10,298,849 B2
(45) Date of Patent: May 21, 2019

(54) IMAGING APPARATUS AND CONTROL METHOD THEREOF

(71) Applicant: SAMSUNG MEDISON CO., LTD., Hongcheon-gun, Gangwon-Do (KR)

(72) Inventors: Jun Sang Yoo, Suwon (KR); Mi Ae Byun, Seongnam-si (KR)

(73) Assignee: SAMSUNG MEDISON CO., LTD., Hongcheon-Gun, Gangwon-Do (KR)

(*) Notice: Subject to any disclaimer, the term of this patent is extended or adjusted under 35 U.S.C. 154(b) by 0 days.

(21) Appl. No.: 14/798,238

(22) Filed: Jul. 13, 2015

(65) Prior Publication Data
US 2016/0014344 A1 Jan. 14, 2016

(30) Foreign Application Priority Data
Jul. 11, 2014 (KR) .................. 10-2014-0087255

(51) Int. Cl.
*G06T 17/00* (2006.01)
*H04N 5/232* (2006.01)
(Continued)

(52) U.S. Cl.
CPC ......... *H04N 5/23293* (2013.01); *A61B 6/463* (2013.01); *A61B 6/467* (2013.01); *A61B 8/463* (2013.01); *A61B 8/467* (2013.01); *G06F 19/00* (2013.01); *G06F 19/321* (2013.01); *G06K 9/00214* (2013.01); *G06T 19/20* (2013.01); *G16H 40/63* (2018.01); *H04N 5/23229* (2013.01); *A61B 5/055* (2013.01); *A61B 6/461* (2013.01); *A61B 6/469* (2013.01);
(Continued)

(58) Field of Classification Search
CPC ......... G06T 17/20; G06T 19/00; G06T 17/00; G06T 17/10; G07T 17/005
USPC ........................................ 345/420
See application file for complete search history.

(56) References Cited

U.S. PATENT DOCUMENTS 5,795,296 A * 8/1998 Pathak ............. A61B 5/1075
600/443
7,876,934 B2 * 1/2011 Georgescu ......... G06K 9/6255
128/922
(Continued)

FOREIGN PATENT DOCUMENTS

GB 2407636 A 5/2005
JP 2006-020750 A 1/2006
(Continued)

OTHER PUBLICATIONS

Extended European Search Report issued in Application No. 15152297.6 dated Nov. 25, 2015.
(Continued)

*Primary Examiner* — Gordon G Liu
(74) *Attorney, Agent, or Firm* — Morgan Lewis & Bockius LLP

(57) ABSTRACT

Disclosed herein is an imaging apparatus including: an image producer configured to produce an image of an object; and an image information generator configured to identify the object, to receive geometry change information for the image of the object, and to generate extraction information corresponding to a geometry image of the object changed according to the geometry change information. Accordingly, it is possible to intuitively display a user's desired information.

18 Claims, 21 Drawing Sheets

(a)

(b)

(51) Int. Cl.
  *G16H 40/63*   (2018.01)
  *A61B 6/00*   (2006.01)
  *A61B 8/00*   (2006.01)
  *G06K 9/00*   (2006.01)
  *G06T 19/20*   (2011.01)
  *G06F 19/00*   (2018.01)
  *A61B 8/08*   (2006.01)
  *A61B 5/055*   (2006.01)

(52) U.S. Cl.
  CPC .......... *A61B 6/5217* (2013.01); *A61B 6/5223* (2013.01); *A61B 6/563* (2013.01); *A61B 8/0866* (2013.01); *A61B 8/4405* (2013.01); *A61B 8/461* (2013.01); *A61B 8/469* (2013.01); *A61B 8/483* (2013.01); *A61B 8/523* (2013.01); *A61B 8/5223* (2013.01); *A61B 8/565* (2013.01); *G06T 2200/08* (2013.01)

(56) References Cited

U.S. PATENT DOCUMENTS

| | | |
|---|---|---|
| 2003/0013959 A1 | 1/2003 | Grunwald et al. |
| 2005/0251015 A1 | 11/2005 | Takikawa et al. |
| 2010/0201683 A1 | 8/2010 | Shirahata et al. |
| 2011/0255762 A1* | 10/2011 | Deischinger ........... A61B 8/463 382/131 |
| 2013/0172743 A1 | 7/2013 | Brewer et al. |
| 2013/0173175 A1 | 7/2013 | Jung et al. |
| 2014/0121524 A1 | 5/2014 | Chiang et al. |
| 2014/0181717 A1 | 6/2014 | Lahti et al. |
| 2014/0184587 A1 | 7/2014 | Park et al. |
| 2014/0193336 A1* | 7/2014 | Rousso ............... A61K 51/0476 424/1.65 |
| 2015/0002538 A1* | 1/2015 | Sohn ..................... A61B 8/5223 345/629 |

FOREIGN PATENT DOCUMENTS

| | | |
|---|---|---|
| JP | 2009-153750 A | 7/2009 |
| KR | 10-2012-0046332 A | 12/2012 |
| WO | 2014/092179 A1 | 6/2014 |
| WO | 2014/103664 A1 | 7/2014 |

OTHER PUBLICATIONS

European Office Action issued in Application No. 15 152 297.6 dated Jan. 17, 2018, 6 pages.

European Communication dated Jan. 16, 2019 issued in European Patent Application No. 15152297.6.

* cited by examiner (a)

5 TIMES ZOOM IN
(b)

10 TIMES ZOOM IN
(c)

1/5 ZOOM OUT
(d)

UP-DOWN INVERSION
(e)

LEFT-RIGHT INVERSION
(f)

ROTATION BY 90 DEGREES
(g)

ROTATION BY -90 DEGREES
(h)

MOVEMENT OF CENTER
(i)

(a)  (b)

(c)  (d)

(a)

(b)

(a)            (b)

DISPLAY OFD
(a)

DISPLAY BPD
(b)

610

(a)  (b)  (c)

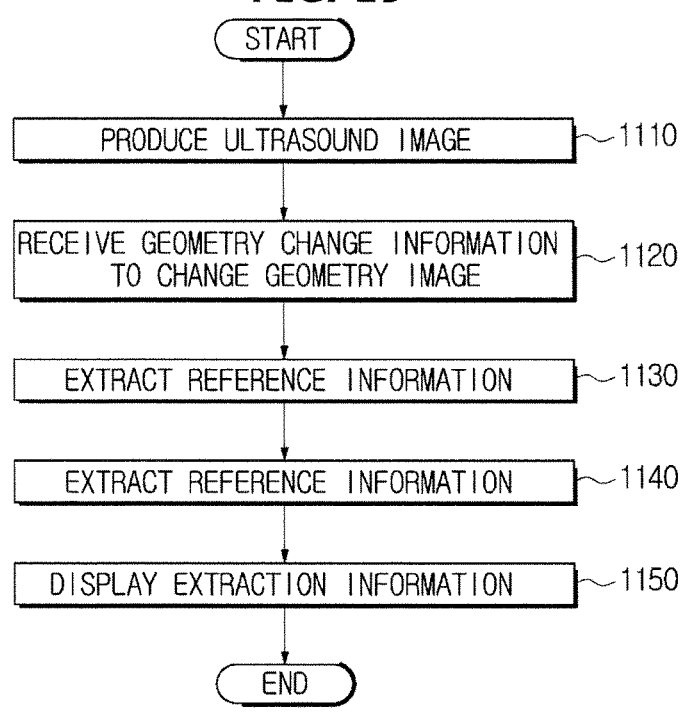

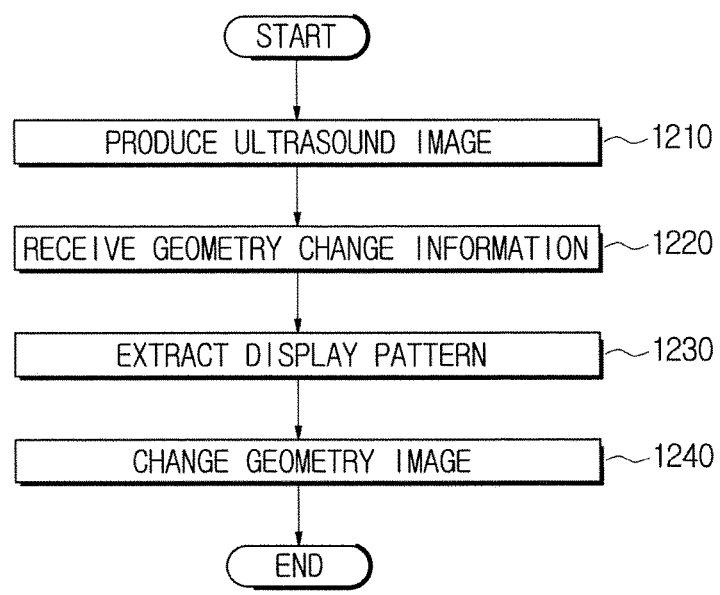

IMAGING APPARATUS AND CONTROL METHOD THEREOF

CROSS-REFERENCE TO RELATED APPLICATION

This application claims the benefit of Korean Patent Application No. 10-2014-0087255, filed on Jul. 11, 2014 in the Korean Intellectual Property Office, the disclosure of which is incorporated herein by reference.

BACKGROUND

1. Field

Embodiments of the present disclosure relate to an imaging apparatus for processing images, and a control method thereof.

2. Description of the Related Art

In general, an imaging apparatus acquires information about a patient and provides the information about the patient in the form of an image. Examples of the imaging apparatus are an X-ray apparatus, an ultrasonic diagnostic apparatus, a computer tomography (CT) scanner, and a magnetic resonance imaging (MRI) apparatus.

The imaging apparatuses have different features. For example, the MRI apparatus allows relatively free image-taking conditions without using radiation, and can provide excellent contrast and various diagnosis information images with respect to soft tissue. However, the MRI apparatus requires a relatively long scanning time compared to other imaging apparatuses, and charges high examination expenses. Meanwhile, the CT apparatus provides images with relatively low resolution and exposes patients to radiation, although it can quickly acquire images and charges low examination expenses.

SUMMARY

Therefore, it is an aspect of the present disclosure to provide an imaging apparatus of differentiating information that is extracted from an image according to geometry change information, and a control method thereof.

It is another aspect of the present disclosure to provide an imaging apparatus of extracting a display pattern corresponding to geometry change information, and changing an image to be displayed according to the display pattern, and a control method thereof.

Additional aspects of the disclosure will be set forth in part in the description which follows and, in part, will be obvious from the description, or may be learned by practice of the disclosure.

In accordance with one aspect of the present disclosure, an imaging apparatus includes: an image producer configured to produce an image of an object; and an image information generator configured to identify the object, to receive geometry change information for the image of the object, and to generate extraction information corresponding to a geometry image of the object changed according to the geometry change information.

The image information generator may include: a storage unit configured to store reference information corresponding to the geometry image of the object; and an extraction information calculator configured to extract the reference information corresponding to the geometry image of the object changed according to the geometry change information, from the storage unit, and to generate extraction information corresponding to the geometry image of the object based on the reference information.

The storage unit may store at least one information among measurement information, landmark information, and Doppler information of the object, as the reference information corresponding to the geometry image of the object.

The image information generator may include an object identifier configured to identify the object based on the image of the object and to generate object information, and the image information generator may generate extraction information corresponding to the object information and the geometry image of the object.

The object identifier may generate, as the object information, information indicating that the image of the object corresponds to at least one of a specific view or a specific area of the object.

The imaging apparatus may further include a display unit configured to display the geometry image of the object and the extraction information.

The imaging apparatus may further include an input unit configured to receive the geometry change information.

The image information generator may receive, as the geometry change information, at least one information among zoom-in/out information, movement information, focal point information, up-down inversion information, left-right inversion information, and rotation information with respect to the image of the object.

The image of the object may be a 3Dimensional (3D) image.

The image of the object may be an ultrasound image.

The image of the object may be a medical image.

In accordance with another aspect of the present disclosure, an imaging apparatus includes: a display unit configured to display an image of an object; a storage unit configured to store reference information corresponding to a geometry image of the image of the object, and a display pattern corresponding to geometry change information of the image of the object; and an image information generator configured to extract the display pattern corresponding to the geometry change information from the storage unit, and to change the image of the object to be displayed, according to the display pattern.

The image information generator may calculate extraction information of the image of the object that is changed according to the display pattern.

The storage unit may store the geometry change information of the image of the object and a display pattern corresponding to the object, and the image information generator may extract the geometry change information and the display pattern corresponding to the object from the storage unit.

The storage unit stores a display pattern corresponding to geometry change information that is at least one information among zoom-in/out information, movement information, focal point information, up-down inversion information, left-right inversion information, and rotation information with respect to the image of the object.

The imaging apparatus may further include an input unit configured to receive the geometry change information.

In accordance with another aspect of the present disclosure, a control method of an imaging apparatus includes: producing an image corresponding to an input signal; receiving geometry change information of the image; extracting reference information corresponding to a geometry image changed according to the geometry change information; and generating extraction information of the geometry image based on the reference information.

The receiving of the geometry change information may include generating object information of the image, and receiving geometry change information of the object, and the extracting of the reference information may include extracting reference information corresponding to a geometry image changed according to the object information and the geometry change information.

The receiving of the geometry change information may include generating, as the object information of the image, information indicating that the image corresponds to at least one of a specific view or a specific area of an object.

The extracting of the reference information may include extracting, as the reference information, at least one information among measurement information, landmark information, and Doppler information of the geometry image.

The control method may further include displaying the extraction information.

BRIEF DESCRIPTION OF THE DRAWINGS

These and/or other aspects of the disclosure will become apparent and more readily appreciated from the following description of the embodiments, taken in conjunction with the accompanying drawings of which:

FIG. 19 is a flowchart illustrating a control method of an imaging apparatus, according to an embodiment of the present disclosure; and FIG. 20 is a flowchart illustrating a control method of an imaging apparatus, according to another embodiment of the present disclosure.

DETAILED DESCRIPTION

Figure 1:
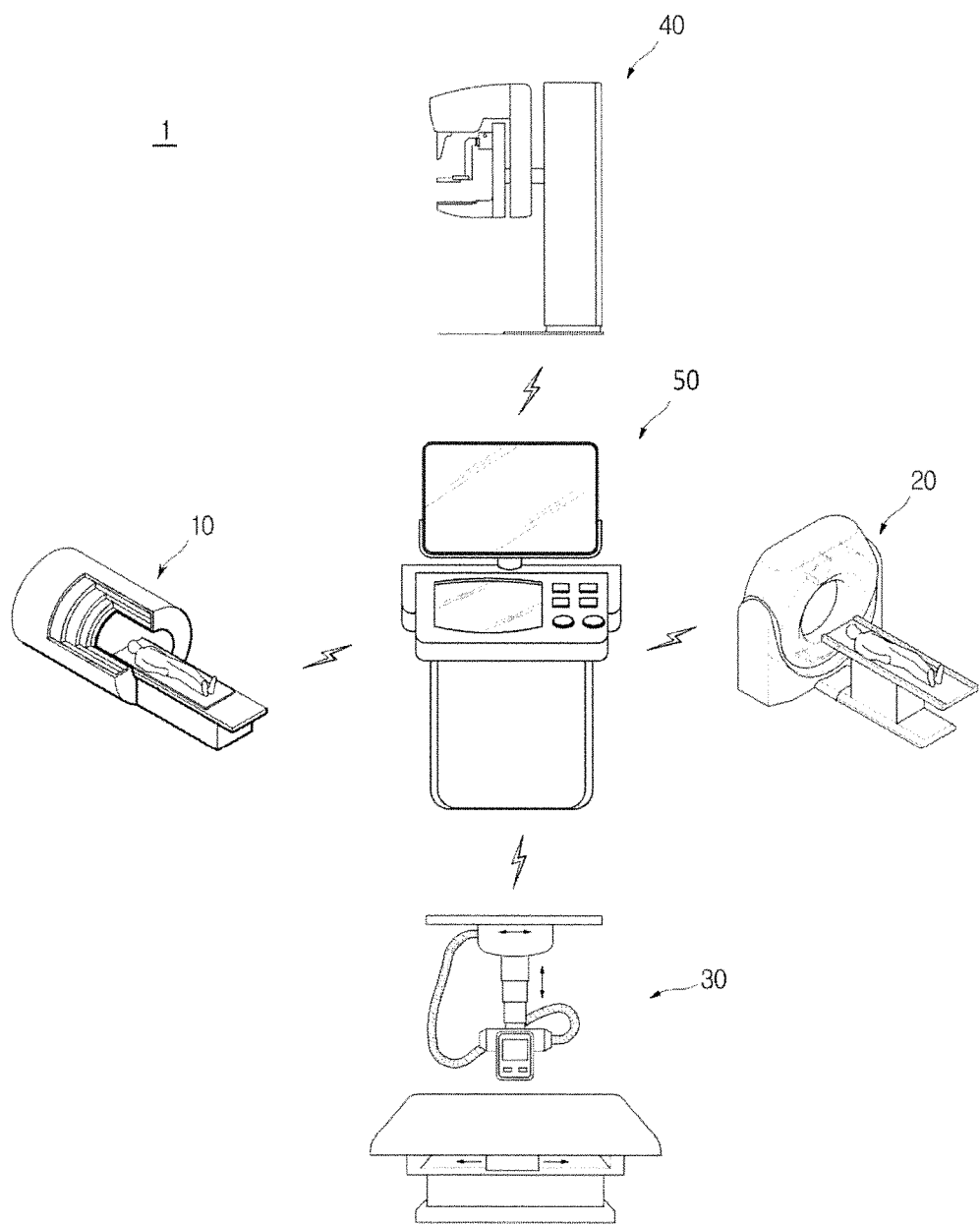
FIG. 1 illustrates an imaging apparatus according to an embodiment of the present disclosure.

Reference will now be made in detail to the embodiments of the present disclosure, examples of which are illustrated in the accompanying drawings, wherein like reference numerals refer to like elements throughout. In the following description, if it is determined that detailed descriptions for related art make the subject matter of the present disclosure obscure unnecessarily, the detailed descriptions will be omitted. It will be understood that, although the terms first, second, etc. may be used herein to describe various components, these components should not be limited by these terms.

Hereinafter, an imaging apparatus and a control method thereof according to embodiments of the present disclosure will be described in detail with reference to the appended drawings.

FIG. 1 illustrates an imaging apparatus according to an embodiment of the present disclosure.

Referring to FIG. 1, an imaging apparatus 1 may include scanners 10, 20, 30, and 40 to acquire images about the inside or outside of an object, and a host unit 50 to combine images received from the scanners 10, 20, 30, and 40.

As shown in FIG. 1, the scanners 10, 20, 30, and 40 may be spaced a predetermined distance away from the host unit 50 of the imaging apparatus 1, and connected to the host unit 50 according to a wired/wireless communication protocol.

For example, the scanner 10 may perform data communication with the host unit 50 according to a Digital Imaging and Communications in Medicine (DICOM) standard. However, a communication method between the scanner 10 and the host unit 50 is not limited to the DICOM standard. The scanners 10, 20, 30, and 40 may be connected to the host unit 50 according to a mobile communication protocol (for example, Global System for Mobile Communication (GSM), Code Division Multiple Access (CDMA), Wideband Code Division Multiple Access (WCDMA), Time Division Multiple Access (TDMA), or Long Term Evolution (LTE)) or according to a short-range communication protocol (for example, Wireless Local Access Network (WLAN), Bluetooth, Zigbee, or Near Field Communication (NFC)).

The scanners 10, 20, 30, and 40 may be used to acquire images about the inside of an object. The scanners 10, 20, 30, and 40 may acquire the images about the inside of the object using radiation, magnetic resonance, or ultrasonic waves. For example, the scanners 10, 20, 30, and 40 may acquire images about the inside of an object using radiation, like a CT scanner, a Position Emission Tomography (PET) scanner, a Single Photon Emission Computed Tomography (SPECT) scanner, or Mammography. Also, the scanners 10, 20, 30, and 40 may acquire images about the inside of an object using magnetic resonance, like a MRI apparatus, or using ultrasonic waves, like an ultrasonic imaging apparatus.

As described above, the scanners 10, 20, 30, and 40 may acquire images of the object using various image acquisition methods each having advantages and disadvantages. For example, CT requires a relatively short scanning time and charges relatively low examination expenses, whereas MRI can acquire high-resolution images although it requires a relatively long scanning time and charges high examination expenses.

Also, according to the inside structure or features of an object, a specific image acquisition method may be preferentially used. For example, if the object is a human body, a specific imaging acquisition method may be preferentially used according to the structure or features of each kind of organ in order to diagnose disease of the human body. Accordingly, acquiring an image of each kind of organ using an image acquisition method that is suitable to scan the kind of organ, and combining images of different kinds of organ acquired using different image acquisition methods may help more accurate diagnosis. In this case, since an image of each kind of organ is acquired using an image acquisition method that is suitable to scan the kind of organ, the time and cost taken to acquire images for diagnosis may be reduced.

In the following description, for convenience of description, it is assumed that images are produced using an ultrasonic scanning method, however, the ultrasonic scanning method can be replaced with another scanning method.

Also, more various kinds of image acquisition methods may be applied to produce images.

Figure 2:
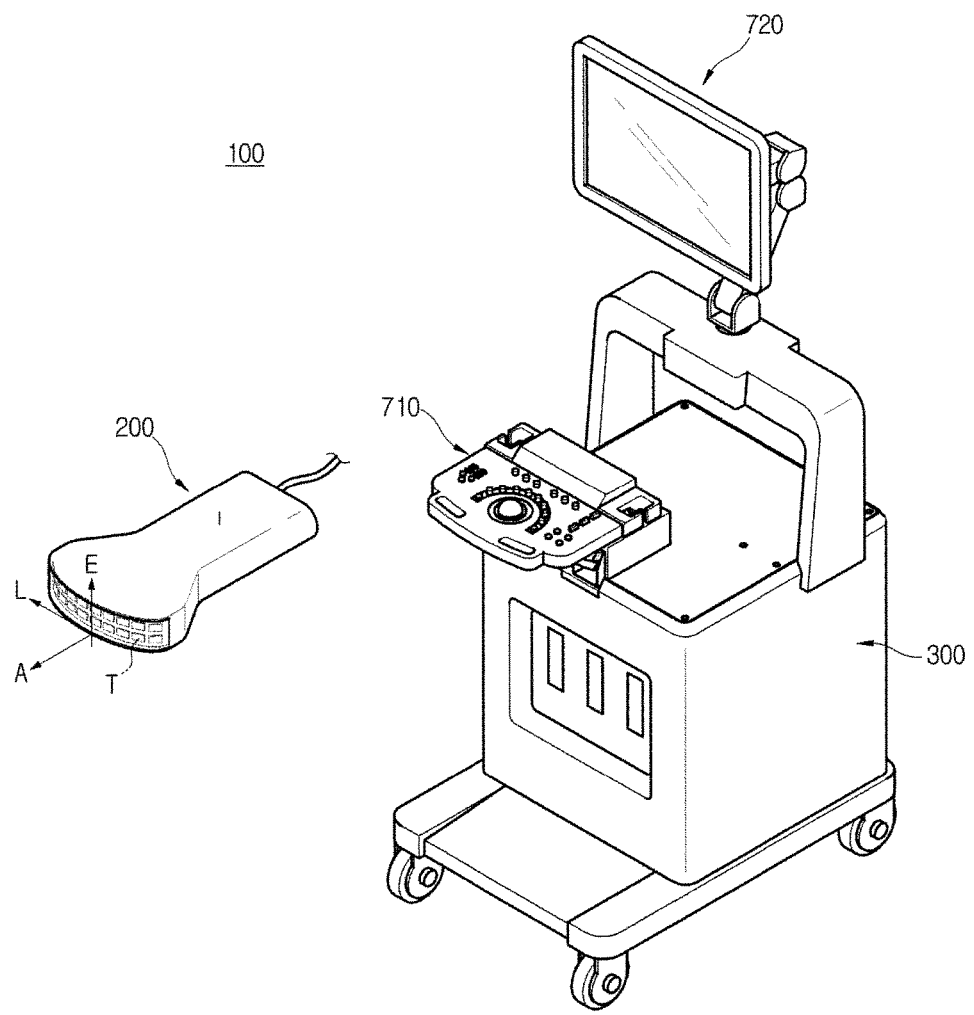
FIG. 2 is a perspective view of an imaging apparatus according to an embodiment of the present disclosure.

FIG. 2 is a perspective view of an imaging apparatus according to an embodiment of the present disclosure.

Referring to FIG. 2, an imaging apparatus 100 may include a probe 200, a main body 300, an input unit 710, and a display unit 720.

The probe 200 may be connected to one end of a cable. The other end of the cable may be connected to a male connector (not shown). The male connector connected to the other end of the cable may be physically coupled with one of female connectors of the main body 300.

The probe 200 may include one or more transducers T. The probe 200 may transmit ultrasound signals to an object, and receive echo ultrasonic waves reflected from the object, using the transducers T. As illustrated in FIG. 2, the transducers T may be arranged in at least one row in one end of the probe 200.

The object may be a human's or animal's body part, or tissue in a body part, such as vessels, bonds, and muscles. However, the object is not limited to the above-mentioned body part or tissue, and may be anything whose inner structure can be imaged by the imaging apparatus 100.

Three directions forming right angles with respect to the center of the transducers T can be defined as an axial direction A, a lateral direction L, and an elevation direction E, respectively. More specifically, a direction in which ultrasonic waves are irradiated is defined as an axial direction A, a direction in which the transducers T form at least one row is defined as a lateral direction L, and the remaining direction perpendicular to the axial direction A and the lateral direction L is defined as an elevation direction E.

The probe 200 of the imaging apparatus 100 may correspond to one of the scanners 10, 20, 30, and 40 of the imaging apparatus 1 of FIG. 1.

The main body 300 may accommodate main components (for example, a transmission signal generator) of the imaging apparatus 100. If an operator inputs an ultrasonic diagnosis command, the transmission signal generator may generate a transmission signal, and transfer the transmission signal to the probe 200.

The main body 300 may include one or more female connectors (not shown). The male connector (not shown) connected to the cable may be physically coupled with one of the female connectors so that signals are transmitted and received between the main body 300 and the probe 200. For example, a transmission signal generated by the transmission signal generator may be transferred to the probe 200 through the cable and the male connector connected to a female connector of the main body 300.

A plurality of casters for fixing the imaging apparatus 100 at a predetermined position or moving the imaging apparatus 100 in a predetermined direction may be provided on the bottom part of the main body 300.

The input unit 710 allows a user to input a command related to an operation of the imaging apparatus 100. For example, a user may input an ultrasonic diagnosis start command, a command for selecting an area to be diagnosed, a command for selecting a diagnosis type, and a command for selecting a display mode of an image to be output, through the input unit 710.

Also, the input unit 710 may receive geometry change information from a user, wherein the geometry change information may include zoom-in/out information, up-down inversion information, left-right inversion information, and rotation information of an ultrasound image.

Figure 3A:
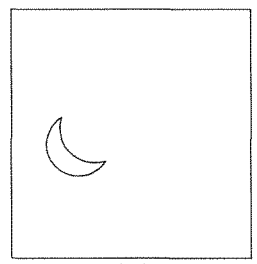
FIGS. 3A and 3B show examples of ultrasound images that are displayed according to geometry change information.
Figure 3A:
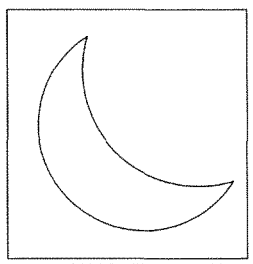
Figure 3A:
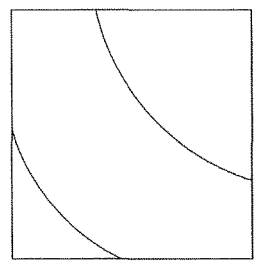
Figure 3A:
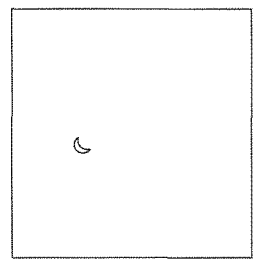
Figure 3A:
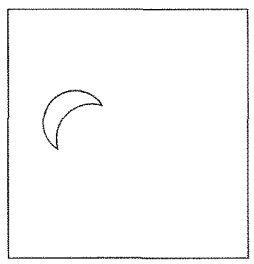
Figure 3A:
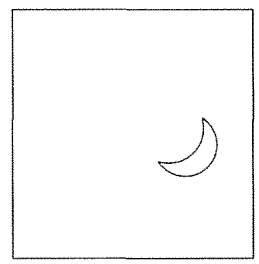
Figure 3A:
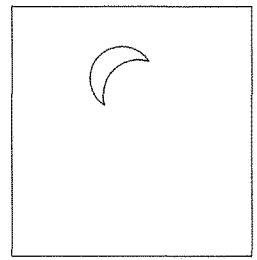
Figure 3A:
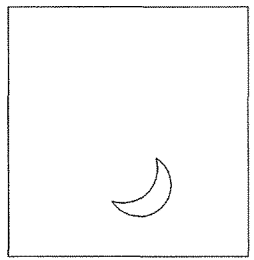
Figure 3A:
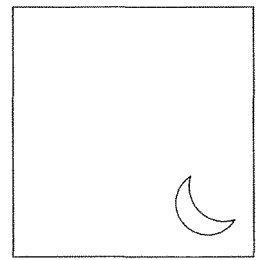
Figure 3B:
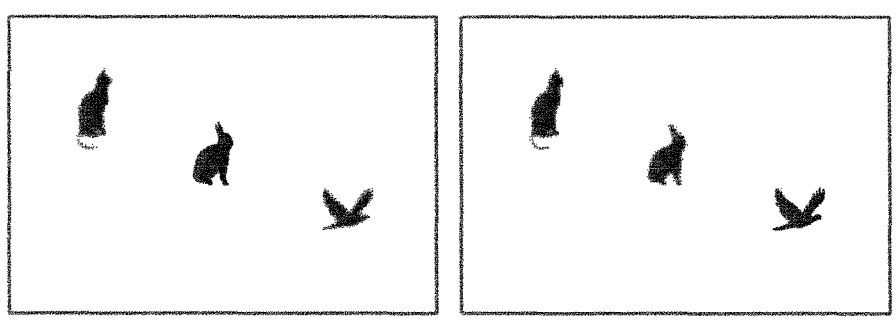
Figure 3B:
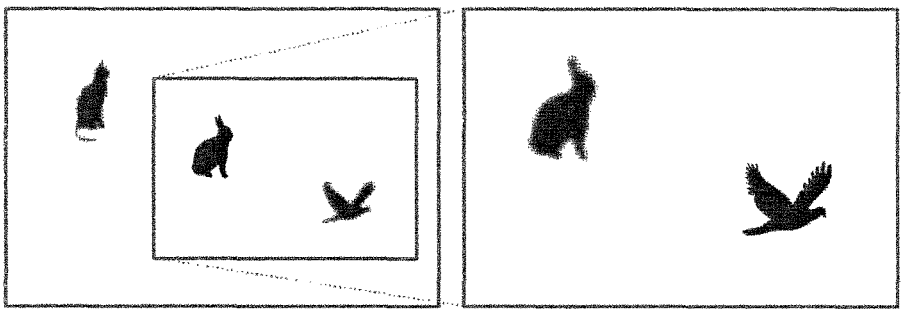

FIGS. 3A and 3B show examples of ultrasound images that are displayed according to geometry change information.

For example, referring to FIG. 3A, a user may input zoom-in/out information through the input unit 710 to zoom in or out an ultrasound image (a) (see, (b), (c) and (d)). Also, the user may input up-down inversion information to invert the ultrasound image (a) in an up-down direction (see (e)), input left-right inversion information to invert the ultrasound image (a) in a left-right direction (see (f)), and input rotation information to rotate the ultrasound image (a) by 90 degrees or by −90 degrees (see (g) and (h)). Also, the user may input movement information through the input unit 710 to move the center of the ultrasound image (a) (see (i)).

Referring to FIG. 3B, the user may input focal point information through the input unit 710 to move the focal point of the ultrasound image (a) (see (b)). Also, the user may input zoom-in/out information to zoom in or out an ultrasound image (c) while moving the center and focal point of the ultrasound image (c) (see (d)), as shown in (b) and (i) of FIG. 3A.

A command input through the input unit 710 may be transmitted to the main body 300 through wired/wireless communication.

The user is a person who diagnoses an object using the imaging apparatus 100, and may be a medical professional including a doctor, a radiological technologist, and a nurse. However, the user is not limited to the above-mentioned persons, and may be anyone using the imaging apparatus 100. A display mode for ultrasound images may include an Amplitude mode (A mode), a Brightness mode (B mode), a Doppler mode (D mode), an Elastography mode (E mode), and a Motion mode (M mode).

The input unit 710 may include at least one of a keyboard, a mouse, a trackball, a touch screen, a foot switch, and a foot pedal, although it is not limited to these.

The input unit 710 may be placed in the upper part of the main body 300, as illustrated in FIG. 2. However, if the input unit 710 is configured with a foot switch and a foot pedal, the input unit 710 may be placed around the lower part of the main body 300.

If the input unit 710 is configured with a Graphical User Interface such as a touch screen, that is, if the input unit 710 is softwarily implemented, the input unit 710 may be displayed through the display unit 720 which will be described later.

One or more probe holders for accommodating the probe 200 may be provided around the input unit 710. The user may put the probe 200 into one of the probe holders to safely keep the probe 200 when he/she does not use the imaging apparatus 100.

The display unit 720 may display an image acquired during ultrasonic diagnosis. The display unit 720 may display the image according to a mode selected by the user, and if no mode is selected by the user, the display unit 720 may display the image in a basic mode (for example, the B mode) set in advance by the user.

Also, the display unit 720 may display a geometry image changed according to geometry change information input by a user. Referring again to FIG. 3, if a user inputs 5 times zoom-in information as geometry change information, the display unit 720 may display a 5 times zoomed-in image (b) for a predetermined area of an ultrasound image. If the user inputs up-down inversion information as geometry change information, the display unit 720 may display an up-down inverted image (e) for a predetermined area of an ultrasound image. However, the display unit 720 may display different images (c), (d), (f), (g), (h), and (i) according to different geometry change information, as described above.

Herein, the predetermined area may have been stored in a storage unit (not shown), and may be the center area of an ultrasound image that is to be displayed through the display unit 720. Also, different predetermined areas may have been designated according to geometry change information. That is, the center area of a geometry image that is to be displayed may depend on geometry change information.

Also, the predetermined area may depend on object information. The object information will be described later.

Also, the geometry image is an image that is currently displayed through the display unit 720. The geometry image may be changed according to geometry change information.

FIGS. 4 to 13 show examples of images that are displayed according to geometry change information.

Figure 4:
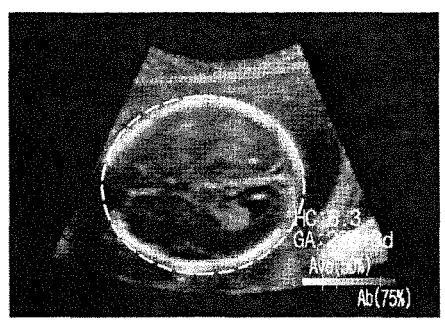
FIGS. 4 to 13 show examples of images that are displayed according to geometry change information.
Figure 4:
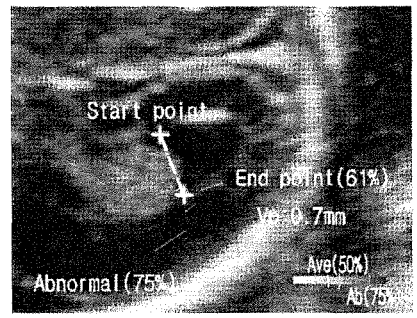

Referring to FIG. 4, if zoom-in/out information for 100 times zooming in an ultrasound image for the brain of a fetus is input, an 100 times zoomed-in ultrasound image in which a center point is a position corresponding to the 100 times zoom-in information may be displayed. Meanwhile, if zoom-in/out information for 300 times zooming in an ultrasound image is input, a 300 times zoomed-in ultrasound image in which a center point is a position corresponding to the 300 times zoom-in information may be displayed.

Also, the display unit 720 may display extraction information corresponding to the geometry image changed according to the geometry change information input by the user. The extraction information may include measurement information, landmark information, brightness information, Doppler information, color information, and history information of the image. The extraction information may have been defined or input in advance by a user. However, the extraction information may be generated automatically based on the ultrasound image.

Also, the extraction information may be differentiated according to object information and the geometry change information. The object information will be described later.

Referring to FIG. 4A, if geometry change information for 100-times zooming in an image for the brain of a fetus is input, measurement information for Head Circumference (HC) and Gestational Age (GA) may be generated as extraction information. Referring to FIG. 4B, if geometry change information for 300-times zooming in an image for the brain of a fetus is input, measurement information (for example, a marker) for Posterior Cerebral Ventricle Diameter (Vp) may be generated as extraction information.

Referring to FIG. 5A, if geometry change information for 100 times zooming in an image for the brain of a fetus is input, landmark information, such as the directions (for example, Anterior (A), Right (Rt), Posterior (P), and Left (Lt)) of the image, the position of Uterus, the position of Cavum Septum Pellucidum (CSP), and the position of skull, may be generated as extraction information. Referring to FIG. 5B, if geometry change information for 100 times zooming in an image for the brain of a fetus is input, landmark information, such as the directions of the image, the position of Choroid Plexus (CP), and the position of Vp, may be generated as extraction information. However, extraction information that is displayed according to geometry change information is not limited to the above-described examples.

If geometry change information for 100 times zooming in a blood vessel image is input, Doppler information may be generated as extraction information, as shown in FIG. 6A, or landmark information such as the position of a blood vessel of the image and measurement information such as blood flow may be generated as extraction information, as shown in FIG. 6B. However, extraction information that is displayed according to geometry change information is not limited to the above-described examples.

Figure 7:
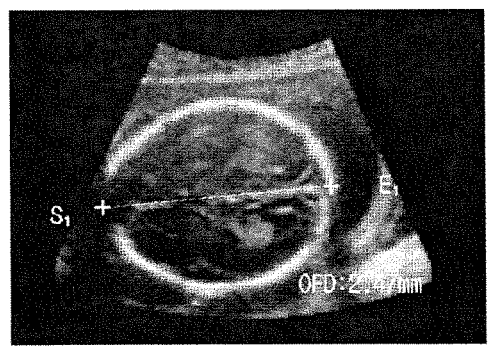
Figure 7:
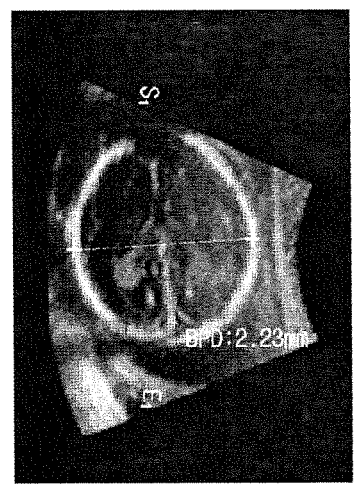

Referring to FIG. 7, if geometry change information for 90 degrees rotating an image for the brain of a fetus in which OccipitoFrontal Diameter (OFD) is generated as measurement information is input, measurement information for BiParietal Diameter (BPD) may be generated as extraction information for a geometry image (b). However, extraction information that is displayed according to geometry change information is not limited to this example.

The measurement information is not limited to the above-described examples, and may include various kinds of measurement information related to the corresponding image, such as BiParietal Diameter (BPD), Abdominal Circumference (AC), Femur Length (FL), the position of Thalamus (T), and Doppler information of blood vessels.

Figure 8:
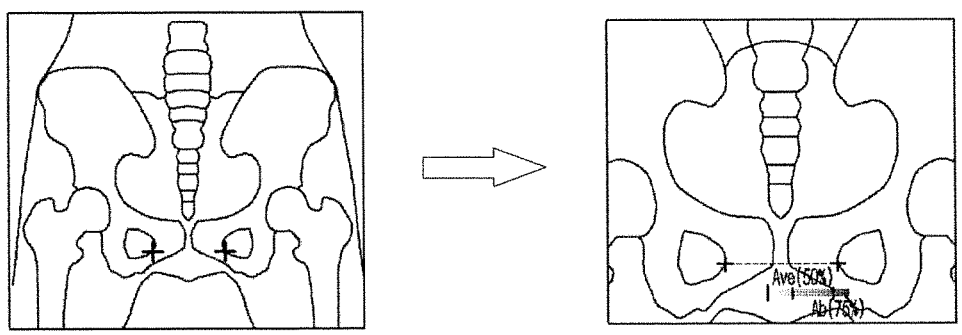
Figure 9:
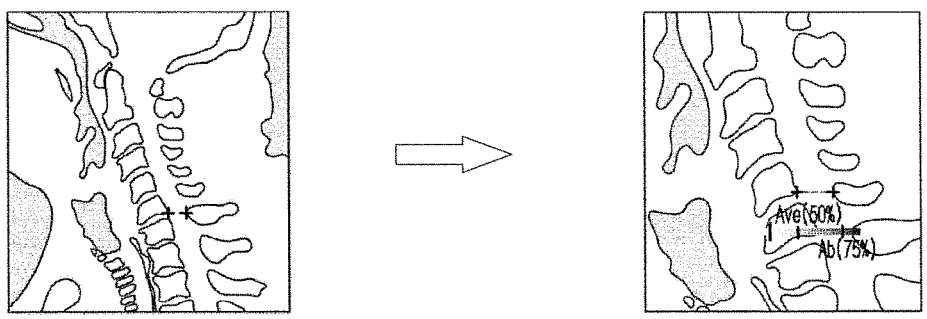
Figure 10:
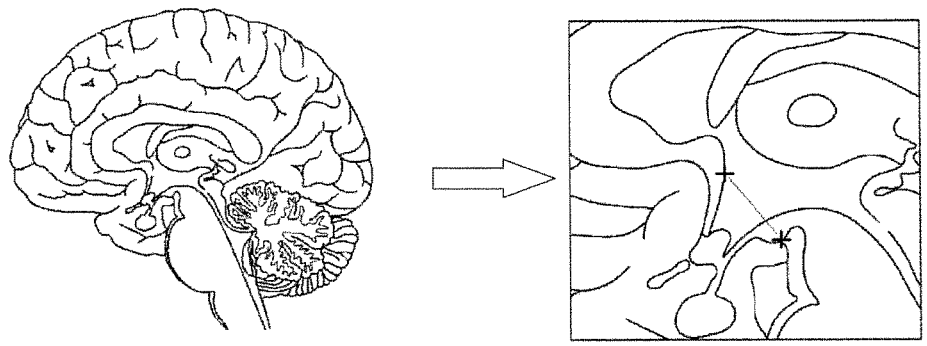
Figure 11:
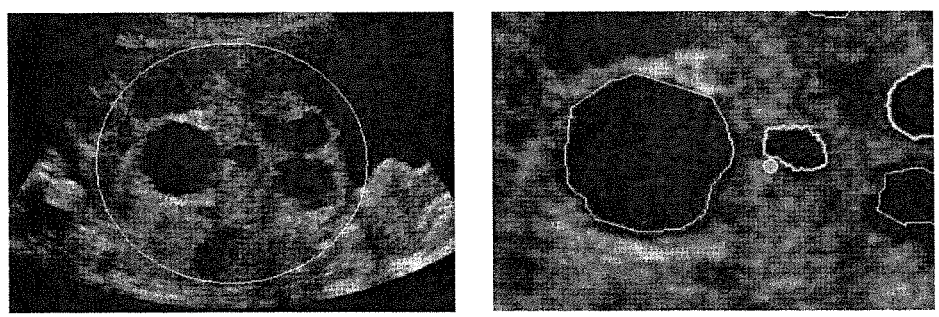
Figure 12:
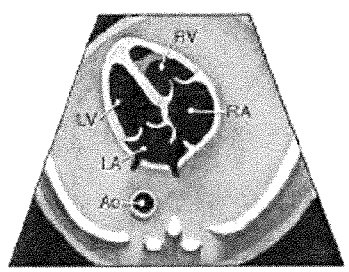
Figure 12:

Also, the image is not limited to an ultrasound image of the brain of a fetus. For example, the image may be an X-ray image of pelvis as shown in FIG. 8, a CT image of backbone as shown in FIG. 9, a MRI image of adult brain as shown in FIG. 10, an ultrasound image that displays follicles as measurement information, as shown in FIG. 11, or an ultrasound image that displays the four chambers of heart with colors, as shown in FIG. 12.

Figure 13:
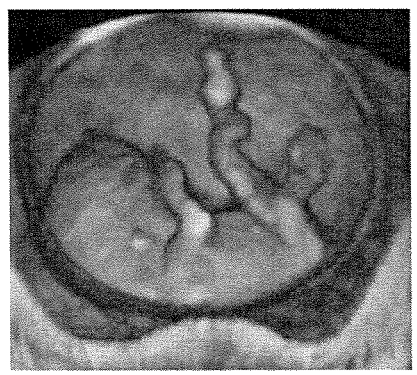
Figure 13:
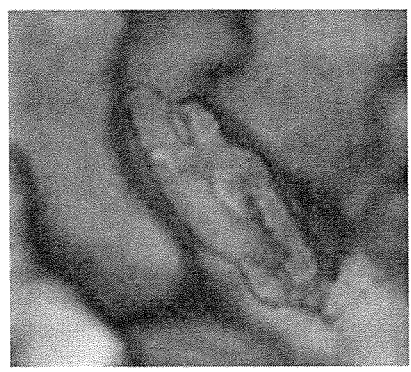

Also, the image may be a 2Dimensional (2D) image or a 3Dimensional (3D) image. For example, the image may be a 3D image that displays the umbilical cord of a fetus with colors according to geometry change information, as shown in FIG. 13.

Referring again to FIG. 2, the display unit 720 may be fixedly coupled with the main body 300. However, the display unit 720 may be detachably coupled with the main body 300. Also, although not shown in FIG. 2, a sub display unit to display applications (for example, a menu or guidance for ultrasonic diagnosis) related to operations of the imaging apparatus 100 may be provided.

The display unit 720 functions to display various information related to the imaging apparatus 100. For example, the display unit 720 may display a first image, a second image, and a combined image produced by combining the first image with the second image. In detail, the display unit 720 may be embodied as a Liquid Crystal Display (LCD), a Light Emitting Diodes (LED) display, an Active Matrix Organic Light Emitting Diodes (AMOLED) display, a flexible display, or a 3D display. Also, the display unit 720 may be a touch screen having both a display function and an input function.

Figure 14:
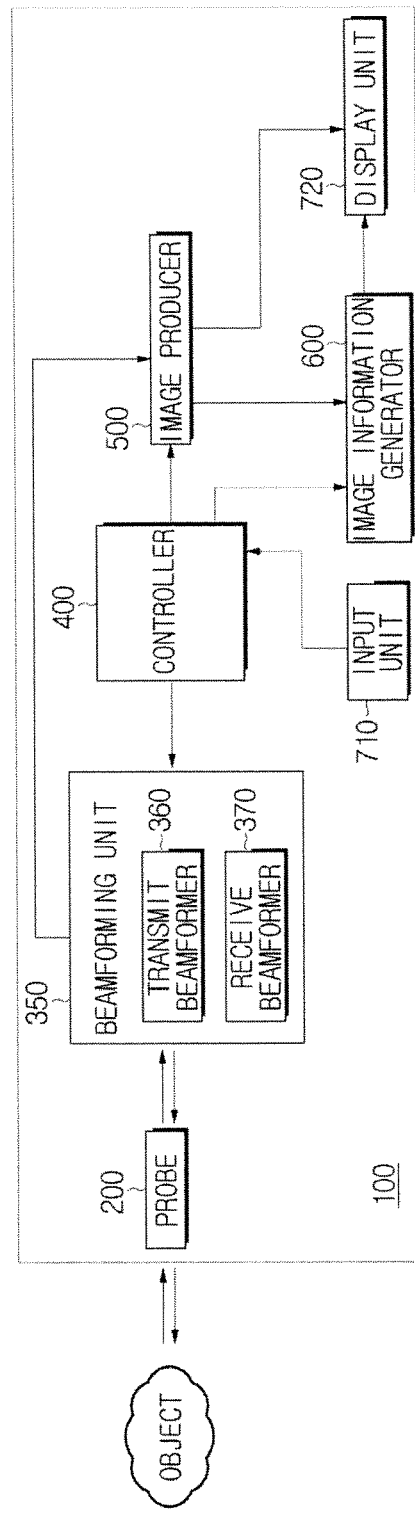
FIG. 14 is a control block diagram of an imaging apparatus according to an embodiment of the present disclosure.

FIG. 14 is a control block diagram of the imaging apparatus 100 according to an embodiment of the present disclosure.

Referring to FIG. 14, the imaging apparatus 100 may produce images about the inside or outside of an object using a probe 200, a beamforming unit 350, a controller 400, an image producer 500, an image information generator 600, the input unit 710, and the display unit 720.

The controller 400 may control overall operations of the imaging apparatus 100. In detail, the controller 400 may generate a control signal for controlling at least one of a transmit beamformer 360, a receive beamformer 370, the image producer 500, and the display unit 720, according to an instruction or command received through the input unit 710. Also, the controller 400 may generate control signals for controlling individual components according to an instruction or a command received from an external device through wired/wireless communication.

The probe 200 may include one or more transducers T to transmit ultrasonic waves to an object, to receive echo ultrasonic waves reflected from the object, and to convert electrical signals into ultrasonic waves and vice versa.

More specifically, if the probe 200 receives current from a power source, such as an external power source or an internal power storage unit (for example, a battery), the individual transducers T vibrate according to the received current to generate ultrasonic waves, and irradiate the ultrasonic waves to an object. The individual transducers T may receive echo ultrasonic waves reflected from the object, and generate current of a frequency corresponding to a vibration frequency while vibrating according to the received echo ultrasonic waves.

Each transducer T may be a magnetostrictive ultrasonic transducer using the magnetostrictive effect of a magnetic material, a capacitive micromachined ultrasonic transducer (cMUT) that transmits and receives ultrasonic waves using vibration of several hundreds or thousands of micromachined thin films, or a piezoelectric ultrasonic transducer using the piezoelectric effect of a piezoelectric material.

The transducers T may be arranged in a linear array, in a convex array, in a phased array, or in a sector array. In this case, the transducers T may be arranged in a line or in a matrix form. If the transducers T are arranged in a line, by swinging the probe 200 in the elevation direction, a plurality of ultrasound images may be acquired. If the ultrasonic transducers T are arranged in a matrix form, by transmitting ultrasonic waves at once, a plurality of ultrasound images may be acquired.

However, the transducers T are not limited to the above-mentioned examples, and may be any other kind of transducers well-known in the art.

The beamforming unit 350 may include the transmit beamformer 360 and the receive beamformer 370. The beamforming unit 350 may convert analog signals into digital signals and vice versa, and adjust time differences with which ultrasonic waves are transmitted from one or more transducers T or time differences with which ultrasonic waves have been received by one or more transducers T.

The ultrasonic waves with adjusted time differences may be focused as a reception signal, and the focused reception signal may be provided to the image producer 500. The signal that is provided to the image producer 500 may be defined as an input signal I.

The image producer 500 may produce an ultrasound image corresponding to the input signal I. The produced ultrasound image may be an Amplitude mode (A mode) image, a Brightness mode (B mode) image, a Doppler mode (D mode) image, an Elastography mode (E mode) image, or a Motion mode (M mode) image, although it is not limited to these. In the following description, it is assumed that the ultrasound image is a B mode image. Herein, the B mode is a diagnosis mode to display a magnitude of an ultrasound echo signal reflected from an object with brightness on a screen. However, the ultrasound image may be displayed on a screen in another mode. Also, the ultrasound image may be a 2D image or a 3D image.

In detail, the image producer 500 may produce an ultrasound image based on an ultrasound signal focused by the receive beamformer 370.

Figure 15:
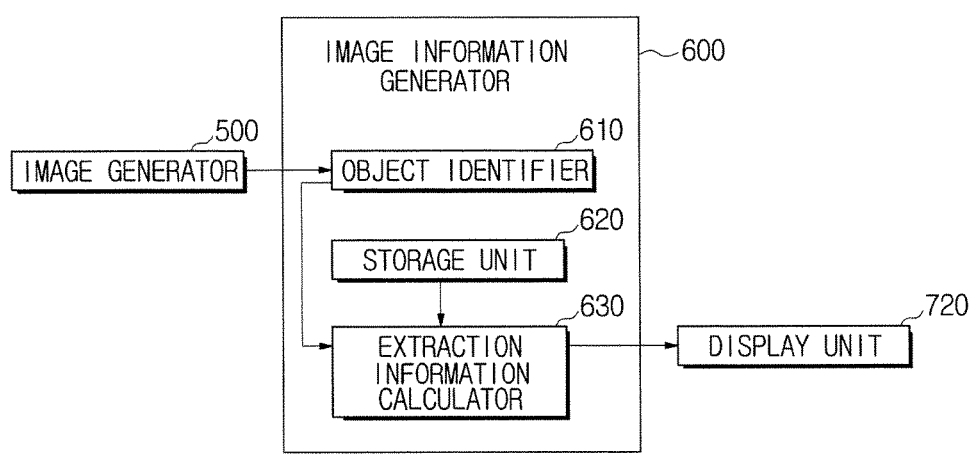
FIG. 15 is a control block diagram of an image information generator according to an embodiment of the present disclosure.

FIG. 15 is a control block diagram of the image information generator 600 according to an embodiment of the present disclosure.

The image information generator 600 may generate various extraction information according to geometry information of an ultrasound image, generated by the image generator 500, wherein the extraction information may include measurement information, landmark information, brightness information, Doppler information, color information, and history information of the ultrasound image.

In order to generate the extraction information, the image information generator 600 may include an object identifier 610 to identify an object and to generate object information, a storage unit 620 in which reference information corresponding to a geometry image of an object is stored, and an extraction information calculator 630 to extract reference information corresponding to a geometry image changed according to input geometry change information from the storage unit 620, and to generate extraction information corresponding to the geometry image based on the extracted reference information.

The object identifier 610 may identify the object, based on the ultrasound image for the object, produced by the image producer 500, to produce object information.

Herein, the object information may be information indicating that the ultrasound image generated by the image producer 500 is a specific object, or that the ultrasound image generated by the image producer 500 is a specific view or a specific area of a specific object. The specific object may be the abdomen, arm, leg, or head of a fetus or adult. However, the specific object may be another body part.

The information indicating that the ultrasound image generated by the image producer 500 is a specific view or a specific area of an object may be, if the object is the brain, information indicating that the ultrasound image is an image of the Mid-Sagittal plane, the Trans-ventricular plane, the Trans-thalamic plane, or the Trans-cerebellar plane. If the object is the heart, the information may be information indicating that the ultrasound image is a Four-chamber view, a Five-chamber view, a Three Vessel view (3VT), a Right ventricular outflow tract (RVOT), a Left ventricular outflow tract (LVOT), a Bicaval View, an Aortic Arch view, a Ductal Arch view, a Short Axis view, or a Long Axis view.

Figure 16:
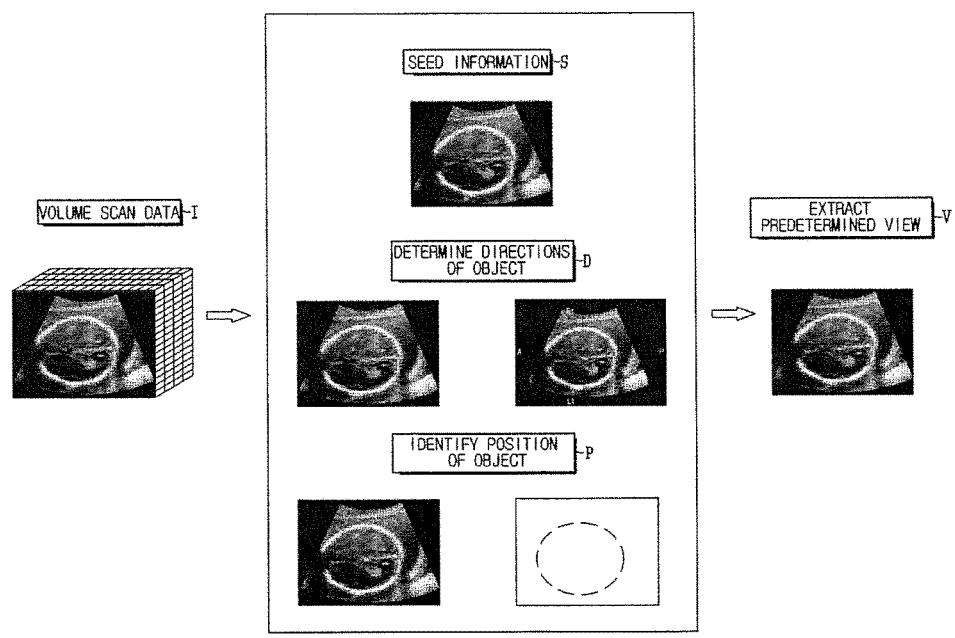
FIG. 16 is a view for describing an example of a process in which an object identifier extracts a specific view.

FIG. 16 is a view for describing an example of a process in which the object identifier 610 extracts a specific view.

Referring to FIG. 16, the object identifier 610 (see FIG. 15) may determine directions D of a specific object from seed information S including initial information that can be obtained from an image (for example, volume scan data I) produced by the image producer 500, identify a position (for example, a position of the brain of a fetus) of the specific object to extract a predetermined view V, and generate object information for the predetermined view V.

However, the image information generator 600 does not necessarily include the object identifier 610. The image information generator 600 may receive object information from an external device through the input unit 710 (see FIG. 15).

The storage unit 620 may store reference information corresponding to a geometry image of an object. The reference information represents extraction information that can be acquired from the geometry image of the object. The reference information may include measurement information, landmark information, and Doppler information.

More specifically, the measurement information may include measurement information (i) including resolution of the geometry image, and the length, width, position coordinates, color, brightness, strength, elasticity, etc. of each part shown in the geometry image, landmark information (ii) representing a predetermined part of the geometry image or directions of the geometry image, and Doppler information (iii) for the geometry image.

Referring again to FIG. 4A, the storage unit 620 may store a HO of a fetus as reference information with respect to a geometry image (a) changed according to 100 times zoom-in information, and referring to FIG. 4B, the storage unit 620 may store ultrasonic wave velocity Vp as reference information with respect to a geometry image (b) changed according to 300 times zoom-in information.

Referring again to FIG. 5A, the storage unit 620 may store directions Rt, A, P, and Lt of a geometry image (a) and a position of skull as reference information with respect to the geometry image (a) changed according to 100 times zoom-in information, and referring to FIG. 5B, the storage unit 620 may store the directions Rt, A, P, and Lt of a geometry image (b) and a position of brain tumor CP as reference information with respect to the geometry image (b) changed according to 300 times zoom-in information.

Also, referring to FIG. 6A, the storage unit 620 may store Dopper information as reference information with respect to a geometry image (a) changed according to 100 times zoom-in information, and referring to FIG. 6B, the storage unit 620 may store a position of a blood vessel and measurement information as reference information with respect to a geometry image (b) changed according to 300 times zoom-in information.

Figure 5:
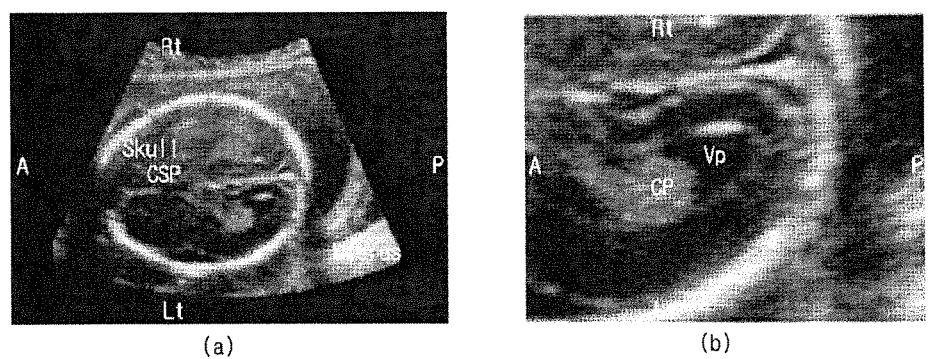
Figure 6:
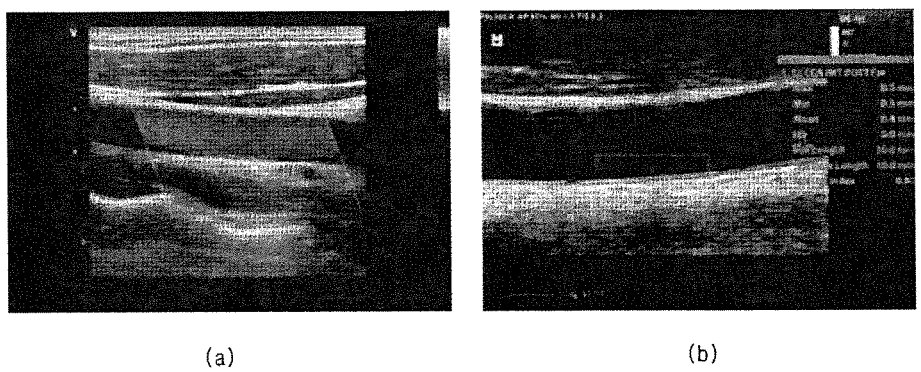

However, the reference information shown in FIGS. 4, 5, and 6 may be only exemplary, and the reference information may include measurement information, landmark information, and Doppler information.

Also, the storage unit 620 may further store object information received from the object identifier 610 or an external device.

According to another embodiment, the storage unit 610 may store a display pattern corresponding to object information/object and geometry change information.

Herein, the display pattern is the center of a geometry image, designated according to one or more geometry change information. However, the display pattern is not limited to the center of a geometry image, and may be a direction of a geometry image. Details for the display pattern will be described later.

Also, the storage unit 610 may be provided outside the image information generator 600, and store programs for performing overall operations of the controller 400, and ultrasound images and geometry images produced by the image producer 500. The storage unit 620 may include a program area and a data area.

The program area may store Operating System (OS) that boots up programs to control overall operations of the imaging apparatus 100. The program area may include programs for operations of the controller 400.

The data area may store data that is generated when the imaging apparatus 100 is used. The data area may store object information, display patterns, reference information, extraction information, and data.

The storage unit 620 may be a cache, Read Only Memory (ROM), Programmable Read Only Memory (PROM), Erasable Programmable Read Only Memory (EPROM), a non-volatile memory device such as flash memory, a volatile memory device such as Random Access Memory (RAM), Hard Disk Drive (HDD), or Compact Disc Read-Only Memory (CD-ROM). However, the storage unit 620 is not limited to the aforementioned devices.

The extraction information calculator 630 may extract reference information corresponding to a geometry image changed according to geometry change information, from the storage unit 620, and generate extraction information corresponding to the geometry image based on the reference information. The extraction information calculator 630 may generate different extraction information according to object information and the geometry image.

That is, the extraction information calculator 630 may generate extraction information corresponding to object information and a geometry image. Herein, the extraction information may include measurement information, landmark information, brightness information, Doppler information, color information, and history information for each part of a geometry image changed by geometry change information input by a user. The extraction information may have been defined or input in advance by a user, or the extraction information may be generated automatically based on the geometry image.

More specifically, the measurement information may include measurement information (i) including resolution of the geometry image, and the length, width, position coordinates, color, brightness, strength, elasticity, etc. of each part shown in the geometry image, landmark information (ii) representing a predetermined part of the geometry image or directions of the geometry image, and Doppler information (iii) for the geometry image.

More specifically, the extraction information calculator 630 may extract reference information corresponding to object information and a geometry image from the storage unit 620, calculate and generate extraction information according to the extracted reference information, and provide the generated extraction information to the display unit 720.

For example, referring again to FIG. 4, if the object is "the brain of a fetus" and the "Trans-ventricular plane" of the brain is generated as object information, the extraction information calculator 630 that receives 100 times zoom-in information as geometry change information may extract reference information corresponding to the "Trans-ventricular plane" of the brain and the "100 times zoom-in information" from the storage unit 620. At this time, the reference information may be HC and GA.

Successively, the extraction information calculator 630 may calculate a position and circumference of the brain from the geometry image, based on the extracted reference information. As a result, the HC denoted by a dotted line may be calculated as 6.3 mm, and the GA may be calculated as 22 weeks and 3 days to generate extraction information. The extraction information may be provided to the display unit 720.

Meanwhile, according to another embodiment, the image information generator 600 may extract a display pattern corresponding to object information and geometry change information from the storage unit 620, and change an image to be displayed according to the extracted display pattern. More specifically, the image information generator 600 may change the center, direction, etc. of a geometry image to be displayed, according to the extracted display pattern.

Figure 17:
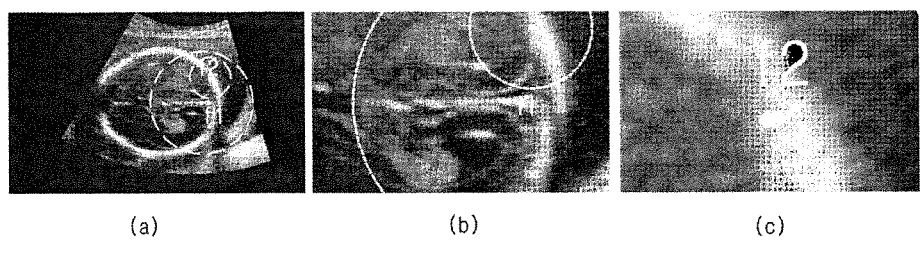
FIG. 17 shows examples of geometry images that are displayed according to display patterns.

FIG. 17 shows examples of geometry images that are displayed according to display patterns.

For example, if 100 times zoom-in information is input, an area f1 of FIG. 17A may be stored as a display pattern (see FIG. 17B), and if 300 times zoom-in information is input, an area f2 of FIG. 17A may be stored as a display pattern (see FIG. 17C).

If the 100 times zoom-in information is input, the image information generator 600 may produce a geometry image whose center is the area f1, according to the display pattern (see FIG. 7B), and if the 300 times zoom-in information is input, the image information generator 600 may produce a geometry image whose center is the area f2, according to the display pattern (see FIG. 17C). The geometry image may be displayed through the display unit 720.

In this case, the image information generator 600 may generate extraction information of an image that is changed according to a display pattern, as shown in FIGS. 4 to 12. The extraction information has been described above, and accordingly, a detailed description thereof will be omitted.

Meanwhile, the image information generator 600 may further include a center point detector (not shown) to generate information about a center point f of an image.

Figure 18:
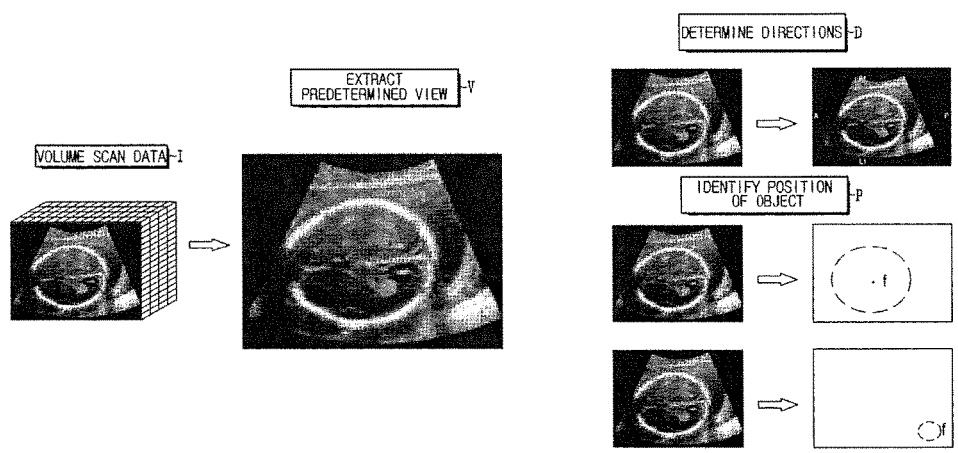
FIG. 18 is a view for describing an example of a method in which a center point detector generates information of a center point f of an image.

FIG. 18 is a view for describing an example of a method in which the center point detector generates information about a center point f of an image.

Referring to FIG. 18, the center point detector may extract a view V from an image (for example, volume scan data I) produced by the image producer 500, determine directions D of the view V, and identify a position P of a specific object from the view W, thereby generating information about a center point f of the object. The generated information about the center point f of the object may be stored as a display pattern in the storage unit 620.

FIG. 19 is a flowchart illustrating a control method of the imaging apparatus 100, according to an embodiment of the present disclosure.

Referring to FIGS. 14, 15, and 19, the imaging apparatus 100 may produce an ultrasound image corresponding to an input signal I received through the beamforming unit 350, in operation 1110. The produced ultrasound image may be an A-mode image, a B-mode image, a D-mode image, an E-mode image, or a M-mode image. However, the ultrasound image is not limited to the aforementioned images. In the following description, it is assumed that the ultrasound image is a B-mode image. Herein, the B mode is a diagnosis mode to display a magnitude of an ultrasound echo signal reflected from an object with brightness on a screen. However, the ultrasound image may be displayed on a screen in another mode. Also, the ultrasound image may be a 2D image or a 3D image.

The ultrasound image may be displayed through the display unit 720.

Successively, the imaging apparatus 100 may receive geometry change information from a user or the input unit 710 to change a geometry image, in operation 1120. The geometry change information may include zoom-in/out information, up-down inversion information, left-right inversion information, and rotation information of the ultrasound image. Herein, the geometry change means a change of an ultrasound image, changed by zooming in/out, translation, rotation, or change of a geometry matrix of the ultrasound image. Also, the geometry image is an image that is currently displayed through the display unit 720, and the geometry image may be changed according to geometry change information.

Then, the imaging apparatus 100 may extract reference information corresponding to object information and the geometry image from the storage unit 620 or an external device, in operation 1130.

Here, the object information may be information indicating that the produced ultrasound image is a specific object or that the produced ultrasound image is a predetermined view or a predetermined area of a specific object. The specific object may be the abdomen, arm, leg, or head of a fetus or adult. However, the specific object may be another body part.

The object information may be input by a user, or generated by the object identifier 610 which is a separate component. Also, the object information may have been stored in advance in the storage unit 620.

The reference information represents extraction information that can be acquired from the geometry image of the object, and may include measurement information, landmark information, and Doppler information.

The object information and the reference information have been described above, and accordingly detailed descriptions thereof will be omitted.

Then, the imaging apparatus 100 may generate extraction information of the geometry image according to the reference information, in operation 1140. More specifically, the imaging apparatus 100 may specify an object to be calculated from the geometry image, based on the extracted reference information, and generate calculated values as extraction information.

Successively, the imaging apparatus 100 may display the extraction information of the geometry image, in operation 1150.

That is, the imaging apparatus 100 may differentiate extraction information to be displayed, according to geometry change information received from a user.

FIG. 20 is a flowchart illustrating a control method of the imaging apparatus 100, according to another embodiment of the present disclosure.

Referring to FIGS. 14 and 20, the imaging apparatus 100 may produce an ultrasound image corresponding to an input signal (I) received through the beamforming unit 350, in operation 1210. The produced ultrasound image may be an A-mode image, a B-mode image, a D-mode image, an E-mode image, or a M-mode image. However, the ultrasound image is not limited to the aforementioned images. In the following description, it is assumed that the ultrasound image is a B-mode image. Herein, the B mode is a diagnosis mode to display a magnitude of an ultrasound echo signal reflected from an object with brightness on a screen. However, the ultrasound image may be displayed on a screen in another mode. Also, the ultrasound image may be a 2D image or a 3D image.

The ultrasound image may be displayed through the display unit 720.

Successively, the imaging apparatus 100 may receive geometry change information from a user, in operation 1220. The geometry change information may include zoom-in/out information, up-down inversion information, left-right inversion information, and rotation information of the ultrasound image. Herein, the geometry change means a change of an ultrasound image, changed by zooming in/out, translation, rotation, or change of a geometry matrix of the ultrasound image.

Then, the imaging apparatus 100 may extract a display pattern corresponding to object information and the geometry image, in operation 1230. Herein, the display pattern is the center of a geometry image, designated according to one or more geometry change information. However, the display pattern is not limited to the center of a geometry image, and may be directions of a geometry image.

Then, the imaging apparatus 100 may change a geometry image to be displayed, according to the extracted display pattern, in operation 1240. More specifically, the imaging apparatus 100 may extract a display pattern corresponding to the received geometry change information to change the center, direction, etc. of the geometry image, and the changed geometry image may be displayed through the display unit 720.

The geometry image, which is currently displayed through the display unit 720, may mean an image that is changed according to geometry change information.

According to the imaging apparatus and the control method thereof as described above, by differentiating extraction information according to geometry change information, it is possible to intuitively display a user' desired information.

Also, according to the imaging apparatus and the control method thereof as described above, by changing an image to be displayed according to geometry change information, a user can observe an area of interest by inputting geometry change information.

The control method of the imaging apparatus 100, as described above, may be implemented as computer-readable code in a computer-readable recording medium. The computer-readable recording medium may include any kind of recording device storing computer-readable data. Examples of the recording medium may include Read Only Memory (ROM), Random Access Memory (RAM), magnetic tape, magnetic disk, flash memory, optical data storage, and the like. In addition, the computer-readable recording medium may be distributed over the computer systems connected over the network, and computer-readable codes may be stored and executed in a distributed manner.

Although a few embodiments of the present disclosure have been shown and described, it would be appreciated by those skilled in the art that changes may be made in these embodiments without departing from the principles and spirit of the disclosure, the scope of which is defined in the claims and their equivalents.

What is claimed is:

1. An imaging apparatus comprising:
   an image producer circuitry configured to produce a first image of an object and a second image which is geometry change information applied to the first image;
   a display configured to display one of the first image or the second image;
   a storage in which reference information representing extract information that is acquirable from one or more geometry images of the object is pre-stored, wherein the reference information includes at least one of measurement information, landmark information, and Doppler information of the object; and
   an image information generator circuitry configured to receive geometry change information for changing the first image to the second image, and extracts reference information corresponding to the second image from the storage, and generate extract information of the second image based on the reference information,
   wherein the display displays one of second extract information corresponding to the second image or first extract information corresponding to the first image,
   wherein the extract information comprises the first extract information or the second extract information,
   wherein the first extract information include at least one type of measurement of information, landmark information of the object, and the second extract information include at least one type of brightness information, Doppler information, color information, and history information of the object.

2. The imaging apparatus according to claim 1, wherein the image information generator circuitry comprises an object identifier configured to identify the object based on the image of the object and to generate object information, and
   wherein the image information generator circuitry generates extract information corresponding to the object information and the geometry image of the object.

3. The imaging apparatus according to claim 2, wherein the object identifier generates, as the object information, information indicating that the image of the object corresponds to at least one of a specific view or a specific area of the object.

4. The imaging apparatus according to claim 1, further comprising a display configured to display the geometry image of the object and the extract information.

5. The imaging apparatus according to claim 1, further comprising an input device configured to receive the geometry change information.

6. The imaging apparatus according to claim 1, wherein the image information generator circuitry receives, as the geometry change information, at least one information among zoom-in/out information, movement information, focal point information, up-down inversion information, left-right inversion information, or rotation information with respect to the image of the object.

7. The imaging apparatus according to claim 1, wherein the image of the object is a 3Dimensional (3D) image.

8. The imaging apparatus according to claim 1, wherein the image of the object is an ultrasound image.

9. The imaging apparatus according to claim 1, wherein the image of the object is a medical image.

10. An imaging apparatus comprising:
    a display configured to display an image of an object;
    a storage in which a display pattern corresponding to geometry change information of the image of the object and including point information of the object is pre-stored; and
    an image information generator circuitry configured to extract the display pattern corresponding to the geometry change information from the storage, and to generate a geometry image whose portion is a point of the object corresponding to the point information which is included in the display pattern,
    wherein the display is configured to display the geometry image, and
    wherein the display displays one image of the object and first extract information of the one image, and displays, in responsive to receiving the geometry change information, the geometry image of the object and second extract information of the geometry image,
    the first extract information and the second extract information is different from each other,
    the pre-stored display pattern is dependent on the object in the image and the geometry change information, and
    using the geometry change information and the pre-stored display pattern, the first and second extract information are obtained from the image and displayed on the display,
    wherein the extract information comprises the first extract information and second extract information,
    wherein the first extract information include at least one type of measurement of information, landmark information of the object, and the second extract information include at least one type of brightness information, Doppler information, color information, and history information of the object.

11. The imaging apparatus according to claim 10, wherein the storage stores the geometry change information of the image of the object and a display pattern corresponding to the object, and wherein the image information generator circuitry extracts the geometry change information and the display pattern corresponding to the object from the storage.

12. The imaging apparatus according to claim 10, wherein a display pattern corresponding to geometry change information that is at least one information among zoom-in/out information, movement information, focal point information, up-down inversion information, left-right inversion information, or rotation information with respect to the image of the object is pre-stored in the storage.

13. The imaging apparatus according to claim 10, further comprising an input device configured to receive the geometry change information.

14. The imaging apparatus according to claim 10, wherein the point information includes center point information, and the portion includes a center of the geometry image.

15. A control method of an imaging apparatus, comprising:

producing a first image of an object and a second image which is geometry change information is applied to the first image corresponding to an input signal;

displaying, by a display, one of the first image or the second image;

receiving geometry change information of the first image and the second image;

extracting, from a storage in which reference information representing extract information that is acquirable from one or more geometry images of the object is pre-stored, reference information corresponding to a geometry image changed according to the geometry change information, wherein the reference information includes at least one of measurement information, landmark information, and Doppler information of the object; and generating extract information of the geometry image based on the extracted reference information, wherein the display displays one image of the object and first extract information of the one image, and displays, in responsive to the receiving the geometry change information, the geometry image of the object and second extract information of the geometry image, the first extract information and the second extract information is different from each other, the pre-stored reference information is dependent on the object in the image and the geometry change information for changing the first image to the second image, and extracts reference information corresponding to the second image from the storage, and generate extract information of the second image based on the reference information, and using the geometry change information and the pre-stored reference information, the first and second extract information are obtained from the image and displayed on the display, wherein the first extract information include at least one type of measurement of information, landmark information of the object, and the second extract information include at least one type of brightness information, Doppler information, color information, and history information of the object.

16. The control method according to claim 15, wherein the receiving of the geometry change information comprises generating object information of the image, and receiving geometry change information of the object, and wherein the extracting of the reference information comprises extracting reference information corresponding to a geometry image changed according to the object information and the geometry change information.

17. The control method according to claim 16, wherein the receiving of the geometry change information comprises generating, as the object information of the image, information indicating that the image corresponds to at least one of a specific view or a specific area of an object.

18. The control method according to claim 15, further comprising displaying the extract information.

* * * * *